US005676135A

United States Patent [19]

McClean

[11] Patent Number: 5,676,135

[45] Date of Patent: Oct. 14, 1997

[54] BREATH SAVER

[76] Inventor: Leon McClean, 2726 Chesire Dr., Baldwin, N.Y. 11510

[21] Appl. No.: 666,953

[22] Filed: Jun. 25, 1996

[51] Int. Cl.[6] .................... A61M 15/00

[52] U.S. Cl. .................... 128/205.22; 128/205.25

[58] Field of Search .................... 128/205.22, 204.18, 128/205.25, 206.21, 206.28, 206.27, 205.24; 190/1, 112, 114; 150/118, 119, 120

[56] References Cited

U.S. PATENT DOCUMENTS

| | | | |
|---|---|---|---|
| 996,135 | 6/1911 | Poe | 128/205.22 |
| 4,685,456 | 8/1987 | Smart | 128/205.22 |
| 5,002,401 | 3/1991 | Blackman | 190/1 |
| 5,243,972 | 9/1993 | Huang | 128/205.22 |
| 5,265,719 | 11/1993 | Wand | 190/112 |
| 5,370,113 | 12/1994 | Parsons | 128/205.22 |

*Primary Examiner*—Vincent Millin
*Assistant Examiner*—William J. Deane, Jr.
*Attorney, Agent, or Firm*—Charles E. Temko

[57] ABSTRACT

A portable emergency respirator comprising a carry case having a compartment therein. An oxygen canister is provided, with a band for retaining the oxygen canister within the compartment of the carry case. A neck strap is on the carry case to be worn about a neck of a person. An elongated tube extends from the oxygen canister. An oxygen mask has a pair of eye pieces and a head strap. The mask is connected to the elongated tube. The head strap is worn about the head of the person with the eye pieces over the eyes. A supply of oxygen can be administered into the nose of the person from the oxygen canister.

2 Claims, 1 Drawing Sheet

BREATH SAVER

BACKGROUND OF THE INVENTION

The instant invention relates generally to respiratory devices and more specifically it relates to a portable emergency respirator, which provides a carry case to be hung from a neck of a person, so as to supply oxygen to that person when needed.

There are available various conventional respiratory devices which do not provide the novel improvements of the invention herein disclosed.

SUMMARY OF THE INVENTION

A primary object of the present invention is to provide a portable emergency respirator that will overcome the shortcomings of the prior art devices.

Another object is to provide a portable emergency respirator, in which a carry case can be suspended from a neck of a person, so that a supply of oxygen from within the carry case can be administered to that person when the need arises.

An additional object is to provide a portable emergency respirator, in which the supply of oxygen is at least one oxygen canister that is coupled to an oxygen hose which is then connected to a nose mask with eye pieces and a head strap, so as to be worn by the person needing the oxygen.

A further object is to provide a portable emergency respirator that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
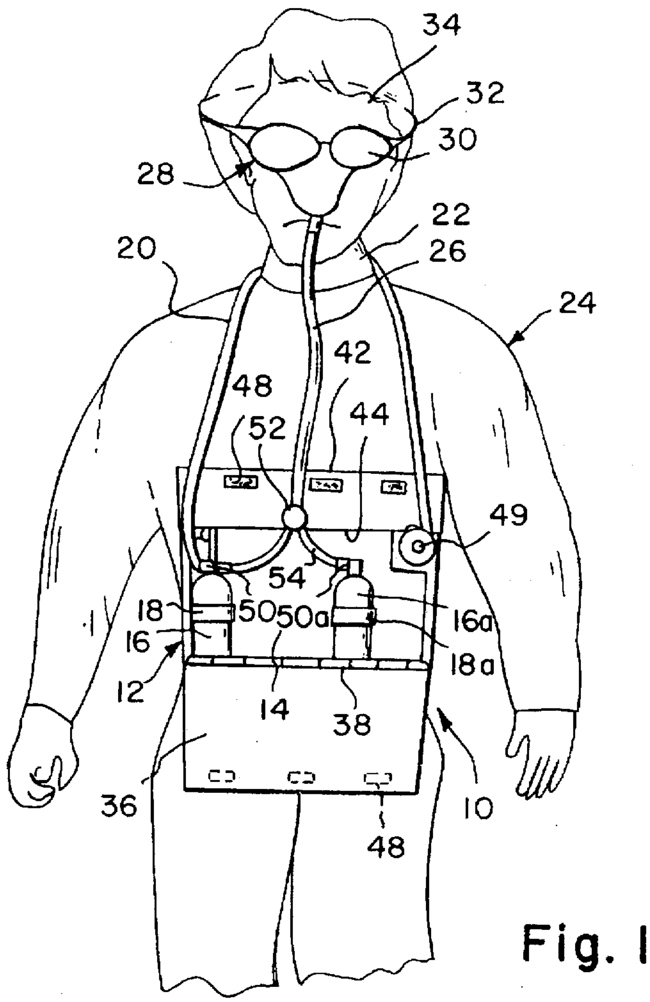
FIG. 1 is a front view of a person wearing and utilizing the instant invention in an open position.
Figure 2:
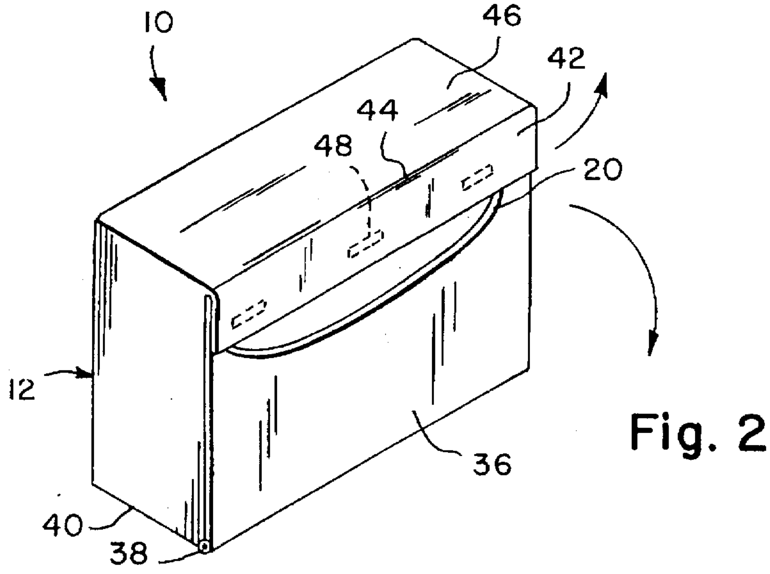
FIG. 2 is a perspective view of the instant invention in a closed stored position.

Turning now descriptively to the drawings, in which similar reference characters denote similar elements throughout the several views, FIGS. 1 and 2 illustrate a portable emergency respirator 10, comprising a carry case 12 having a compartment 14 therein. An oxygen canister 16 is provided, with a band 18 for retaining the oxygen canister 16 within the compartment 14 of the carry case 12. A neck strap 20 is on the carry case 12 to be worn about a neck 22 of a person 24. An elongated tube 26 extends from the oxygen canister 16. An oxygen mask 28 has a pair of eye pieces 30 and a head strap 32. The mask 28 is connected to the elongated tube 26. The head strap 32 is worn about the head 34 of the person 24 with the eye pieces 30 over the eyes. A supply of oxygen can be administered into the nose of the person 24 from the oxygen canister 16.

The carry case 12 includes a lower front flap 36 hinged at 38 to a bottom wall 40. An upper front flap 42 is hinged at 44 to a top wall 46 to overlap the lower front flap 36. A plurality of VELCRO fasteners 48 are for holding the upper front flap 42 closed onto the lower front flap 36.

The strap 20 is extendable from the carry case 12 at a spool 49. When the neck strap 20 is pulled upwardly therefrom it will separate the VELCRO fasteners 48. The upper front flap 42 will lift up and the lower front flap 36 will fall down, allowing the person 24 to have access to a valve 50 for manual actuation of valve 50 on the oxygen canister 16.

An auxiliary oxygen canister **16*a* is also provided. A second band 18*a* is for retaining the auxiliary oxygen canister 16*a* within the compartment 14 of the carry case 12. A two-way valve 52 is connected into the elongated tube 26. An auxiliary tube 54 is connected between the two-way valve 52 and a valve 50*a* of the auxiliary oxygen canister 16*a*. The auxiliary oxygen canister 16*a* can be used when the original oxygen canister 16 is empty, by manually turning the two-way valve 52 to open the auxiliary tube 54 and then manually opening the valve 50*a* on the auxiliary oxygen canister 16*a***.

OPERATION OF THE INVENTION

To use the portable emergency respirator 10, a person 24 simply pulls the neck strap 20 upwardly to separate the VELCRO fasteners 48. The upper front flap 42 lifts up and the front flap 36 falls down. The neck strap 20 is then placed about the neck 22 of the person 24. The mask 28 is put on and the valve 50 opened to allow oxygen to flow from the oxygen canister 16 to the mask 28. When the oxygen canister 16 is empty, the two-way valve 52 can be turned and the valve **50*a* opened to allow oxygen to flow from the auxiliary oxygen canister 26*a* to the mask 28**.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A portable emergency respirator comprising: a carry case having a compartment therein; an oxygen canister; a band for retaining said oxygen canister within said compartment of said carry case; a neck strap on said carry case to be worn about a neck of a person; an elongated tube extending from said oxygen canister; and an oxygen mask having a pair of eye pieces and a head strap, said mask connected to said elongated tube, said head strap being worn about the head of a person with said eye pieces over the eyes, so that a supply of oxygen can be administered into the nose of said person from said oxygen canister; Said case including a lower front flap hinged to a bottom wall, an upper front flap hinged to a top wall to overlap said lower front flap; and a plurality of hook and pile fasteners for holding said upper front flap closed onto said lower front flap; said strap being extendable from said carry case, whereby when said neck strap is pulled upwardly therefrom, it will separate said hook and pile fasteners, so that said upper front flap will lift up and said lower front flap will fall down allowing said person to manually open a valve on said oxygen canister.

2. A portable emergency respirator as recited in claim 1, further including: an auxiliary oxygen canister, a second band for retaining said auxiliary oxygen canister within said compartment of said carry case; a two-way valve connected into said elongated tube; and an auxiliary tube connected between said two-way valve and a valve of said auxiliary oxygen canister so that said auxiliary oxygen canister can be used when said original oxygen canister is empty, by manually turning said two-way valve to open said auxiliary tube and manually opening the valve on said auxiliary oxygen canister.

* * * * *